US00PP19125P2

(12) United States Plant Patent
Zary

(10) Patent No.: US PP19,125 P2
(45) Date of Patent: Aug. 19, 2008

(54) HYBRID TEA ROSE PLANT NAMED 'JACSUMIO'

(50) Latin Name: *Rosa hybrida*
Varietal Denomination: JACsumio

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/824,554

(22) Filed: Jun. 29, 2007

(51) Int. Cl.
*A01H 5/00* (2006.01)

(52) U.S. Cl. ..... Plt./134

(58) Field of Classification Search ..... Plt./134
See application file for complete search history.

(56) References Cited

U.S. PATENT DOCUMENTS

PP7,659 P * 10/1991 Warriner ..... Plt./134
PP15,955 P3 * 9/2005 Zary ..... Plt./134

* cited by examiner

*Primary Examiner*—Wendy C. Haas
(74) *Attorney, Agent, or Firm*—Klarquist Sparkman, LLP

(57) ABSTRACT

Hybrid tea rose plant having flowers with vigorous upright growth habit; long cutting stems; excellent flower form and petal substance; distinctive anise fragrance; non-fading yellow flower coloration; and good resistance to powdery mildew and rust.

1 Drawing Sheet

Genus and species: *Rosa hybrida.*
Variety denomination: 'JACsumio'.

ORIGIN OF THE INVENTION

The present invention relates to a new and distinct variety of a hybrid tea rose plant named 'JACsumio' which was originated by me by crossing the variety 'JACdash' (female parent, U.S. Plant Pat. No. 7,659), with the variety 'DELosol' (male parent, not patented). The parentage of 'DELosolo' is [Peace×Marcelle Gret]×[Velizy seeding].

BACKGROUND OF THE INVENTION

The primary objective of this breeding was to produce a new hybrid tea rose variety having the tall upright growth, bright yellow color and vigor of the female (seed) parent combined with the long stems and good petal substance of the male (pollen) parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Vigorous upright growth habit.
2. Long cutting stems.
3. Excellent flower form.
4. Excellent petal substance.
5. Distinctive anise fragrance.
6. Non-fading yellow flower coloration.
7. Good resistance to powdery mildew and rust.

Asexual reproduction of this new variety by cuttings, as performed at Wasco, Calif., shows that the foregoing characteristics and distinctions come true to form and are established and transmitted through succeeding propagations.

COMPARISON WITH PARENTS

'JACdash' differs from 'JACsumio' in flower color (yellow 21A to B for 'JACdash' versus yellow 13B for open flowers of 'JACsumio').

COMPARISON WITH SIMILAR VARIETY

The closest variety is believed to be 'JACdash' (U.S. Plant Pat. No. 7,659), which has been compared above.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—'JACdash' (U.S. Plant Pat. No. 7,659).

*Pollen parent.*—'DELosol' (not patented). The parentage of 'DELosol' is [Peace×Marcelle Gret]×[Velizy seeding].

FLOWER

Observations made from January 2006 to June 2007 from plants at two to three years of age growing in a garden environment at Somis, Claif.

Blooming habit: Continuous.

Bud:

*Size.*—About 45 mm long and 35 mm in diameter when the petals start to unfurl.

*Form.*—The bud form is long, pointed ovoid.

*Color.*—When sepals first divide, but color is Yellow-Orange Group 15B tipped in Orange Group N25D in cool night weather (below 10° C.). When half blown, the upper sides of the petals are Yellow Group 13B and the lower sides of the petals are Yellow Group 13B.

*Sepals.*—Color: Upper surface: Green Group 138B. Lower surface: Yellow-Green Group 146C sometimes overlain with Greyed-Purple Group 183C. Length: 33 mm. Width: 8 mm. Shape: Subulate. Surface texture: Hoary. Three are three normally to heavily appendaged sepals. There are two unappendaged sepals with hairy edges.

*Receptacle.*—Color: Yellow-Green Group 146A. Shape: Funnel. Size: Medium, about 8 mm long×6 mm in diameter. Surface: Smooth.

*Peduncle.*—Length: Short, averaging about 40 mm. Surface: Glandular. Color: Yellow-Green Group 146A. Strength: Stiff, erect.

Bloom:

*Size.*—Large. Average open diameter is about 12–13 cm.

*Borne.*—Singly.

*Stems.*—Strength: Strong. Average length is about 45–60 cm with a diameter of 7–9 mm.

*Form.*—When first open: High centered. Permanence: Retains its form to the end, but outer petals curl slightly.

*Petalage.*—Number of petals under normal conditions: 30.

*Color.*—The upper sides of the petals are Yellow Group 13B. The reverse sides of the petals are Yellow Group 13B. No observable color spot. The major color on the upper sides is Yellow Group 13B.

*Variegations.*—None observed.

*Discoloration.*—The general tonality at the end of the first day: No change. At the end of the third day: No change. Further aging: No change.

*Fragrance.*—Moderate. Anise.

Petals:

*Texture.*—Thick, leathery.

*Surface.*—Smooth.

*Shape.*—Round.

*Margin.*—Entire.

*Apex shape.*—Obtuse.

*Base shape.*—Rounded.

*Form.*—Tips slightly recurved.

*Arrangement.*—Imbricated.

*Petaloids.*—Number: 3–7. Size: 13–30 mm long×5–25 mm wide.

*Persistence.*—Petals drop off cleanly before drying.

*Lastingness.*—On the plant: Long (about 7 days). As a cut flower: Long (about 9 days).

Reproductive parts:

*Stamens.*—Number: 50–70. Length: 8–12 mm. Anthers: Length: 3–4 mm. Color: Yellow-Orange Group 16B. Arrangement: Regular around styles. Filaments: Color: Orange-Red Group N30A. Length: 4–9 mm. Pollen: Color: Greyed-Orange Group N163A.

*Pistils.*—Number: 40–50. Length: 9–12 mm. Styles: Color: Yellow-Green Group 149D. Length: 8–11 mm. Stigmas: Color: Red Group 41B. Length: 1 mm.

*Hips.*—None observed.

PLANT

*Form.*—Bush.

*Growth.*—Vigorous, upright, branching.

*Age to maturity.*—Two years.

*Mature plant.*—Height: 5½ ft. Width: 4 ft.

Foliage: Number of leaflets on normal mid-stem leaves: 5–7.

*Size.*—Medium. About 12–15 cm long×8–10 cm wide.

*Quantity.*—Normal.

*Color.*—New foliage: Upper side: Greyed-Purple Group 183B. Lower side: Greyed-Red Group 181A. Old foliage: Upper side: Green Group 139A. Lower side: Green Group 143C.

Leaflets:

*Size.*—About 4–6 cm long×3–4 cm wide.

*Shape.*—Pointed oval.

*Base shape.*—Oblique.

*Apex shape.*—Acuminate.

*Texture.*—Leathery, matte.

*Edge.*—Serrated.

*Serrations.*—Single.

*Petiole.*—Color: Yellow-Green Group 147D.

*Petiole rachis.*—Color: Yellow-Green Group 147D. Underside: Prickles, few.

*Auricles.*—Subulate.

*Stipules.*—Length: 20–25 mm.

*Disease resistance.*—Resistant to mildew and rust, susceptible to blackspot under normal growing conditions.

*Pest resistance.*—Not observed.

*Vein color.*—Green Group 139A.

*Venation pattern.*—Reticulate.

Wood:

*New wood.*—Color: Greyed-Purple Group 183C. Bark: Smooth.

*Old wood.*—Color: Green Group 137C. Bark: Smooth.

Prickles:

*Quantity.*—Ordinary, on main canes from base: 25–30 per 150 mm of cane. Ordinary, on laterals from main canes: 25–30 per 150 mm of cane.

*Form.*—Hooked downward.

*Length.*—6–8 mm.

*Color when young.*—Greyed-Purple Group 183B.

*Color when mature.*—Greyed-Orange Group 177A to 177B.

Small prickles:

*Quantity.*—On main stalks: None observed. On laterals: None observed.

Winter hardiness: Hardy to Zone 5.

I claim:

1. A new and distinct variety of hybrid tea rose plant, substantially as herein shown and described, characterized particularly by its vigorous upright growth habit; long cutting stems; excellent flower form and petal substance; distinctive anise fragrance; non-fading yellow flower coloration; and good resistance to powdery mildew and rust.

* * * * *

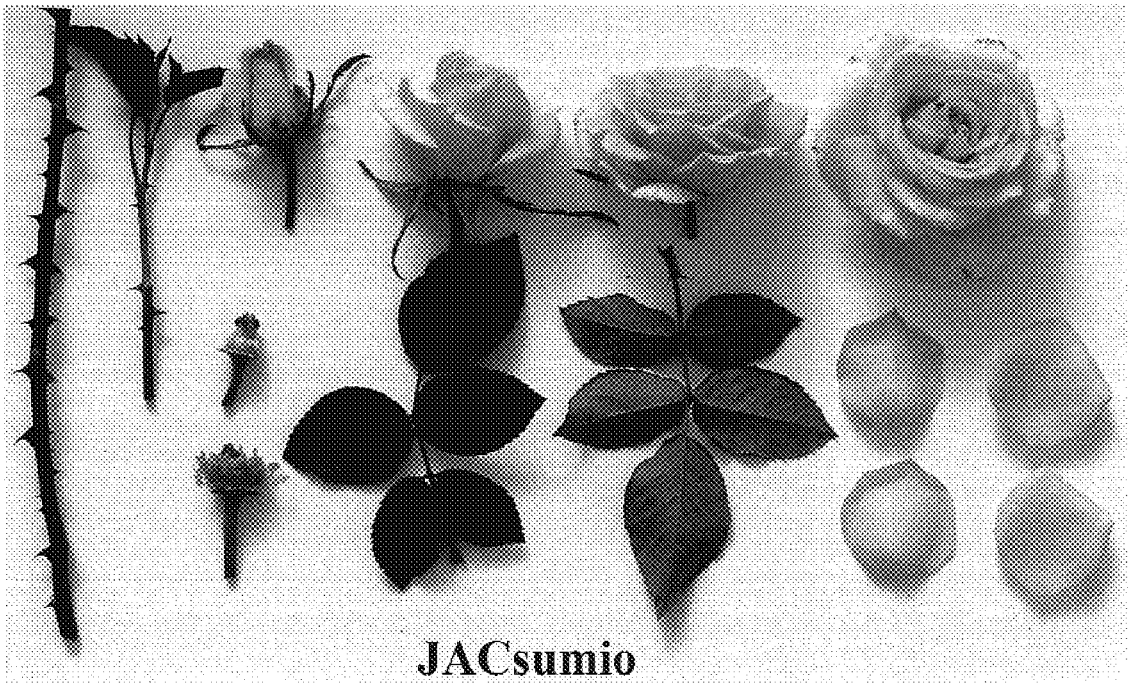
JACsumio

UNITED STATES PATENT AND TRADEMARK OFFICE

CERTIFICATE OF CORRECTION

PATENT NO. : PP19,125 P2
APPLICATION NO. : 11/824554
DATED : August 19, 2008
INVENTOR(S) : Keith W. Zary It is certified that error appears in the above-identified patent and that said Letters Patent is hereby corrected as shown below:

In the Specification:

Column 1, line 11, "'DELosolo'" should read -- 'DELosol' --

Column 3, line 5, "Claif." should read -- Calif. --

Column 3, line 12, "but color" should read -- bud color --

Column 3, line 22, "Three are three", should read -- There are three --

Signed and Sealed this
Twenty-fourth Day of May, 2011

David J. Kappos

David J. Kappos
*Director of the United States Patent and Trademark Office*